US009612236B2

(12) United States Patent
Sabatte et al.

(10) Patent No.: US 9,612,236 B2
(45) Date of Patent: Apr. 4, 2017

(54) MULTI EPITOPE ASSAY

(75) Inventors: Gwenola Sabatte, Eindhoven (NL); Menno Willem Jose Prins, Eindhoven (NL); Toon Hendrik Evers, Eindhoven (NL); Wilhelmina Maria Hardeman, Eindhoven (NL); Joukje Garrelina Orsel, Eindhoven (NL)

(73) Assignee: Koninklijke Philips N.V., Eindhoven (NL)

(*) Notice: Subject to any disclaimer, the term of this patent is extended or adjusted under 35 U.S.C. 154(b) by 0 days.

(21) Appl. No.: 13/704,258

(22) PCT Filed: Jun. 14, 2011

(86) PCT No.: PCT/IB2011/052570
§ 371 (c)(1),
(2), (4) Date: Dec. 14, 2012

(87) PCT Pub. No.: WO2011/158174
PCT Pub. Date: Dec. 22, 2011

(65) Prior Publication Data
US 2013/0095495 A1    Apr. 18, 2013

(30) Foreign Application Priority Data

Jun. 17, 2010 (EP) ..................... 10166390
Nov. 25, 2010 (EP) ..................... 10192505

(51) Int. Cl.
G01N 33/53     (2006.01)
G01N 33/543    (2006.01)

(52) U.S. Cl.
CPC ... *G01N 33/5306* (2013.01); *G01N 33/54306* (2013.01); *G01N 33/54333* (2013.01)

(58) Field of Classification Search
None
See application file for complete search history.

(56) References Cited

U.S. PATENT DOCUMENTS

| 5,599,677 | A  | * | 2/1997  | Dowell et al. | 435/7.4 |
| 6,348,318 | B1 | * | 2/2002  | Valkirs | 435/7.1 |
| 7,776,586 | B2 |   | 8/2010  | Cregan et al. | |
| 8,569,074 | B2 |   | 10/2013 | Zand et al. | |
| 2002/0040000 | A1 | * | 4/2002 | Dworetzky et al. | 514/12 |
| 2002/0155578 | A1 | * | 10/2002 | Szostak et al. | 435/226 |
| 2003/0082568 | A1 | * | 5/2003 | Phan et al. | 435/6 |
| 2004/0023273 | A1 |   | 2/2004  | Puget | |
| 2008/0202933 | A1 | * | 8/2008  | Hu | 204/451 |
| 2009/0036315 | A1 | * | 2/2009  | Labgold et al. | 506/1 |
| 2009/0139867 | A1 |   | 6/2009  | Marziali | |
| 2009/0142772 | A1 |   | 6/2009  | Lau | |
| 2010/0021890 | A1 |   | 1/2010  | Schallmeiner | |
| 2010/0075439 | A1 | * | 3/2010  | Duffy et al. | 436/518 |
| 2010/0200405 | A1 | * | 8/2010  | Lenz | 204/600 |
| 2010/0279272 | A1 |   | 11/2010 | Burrell et al. | |

FOREIGN PATENT DOCUMENTS

| JP | 2001258551 | | 9/2001 |
| WO | WO 0047983 A1 | * | 8/2000 |
| WO | 03065042 A1 | | 8/2003 |
| WO | 2007079149 A2 | | 7/2007 |
| WO | WO 2007079149 A2 | * | 7/2007 |

OTHER PUBLICATIONS

Kwon et al. (Magnetic Bead Based Immunoassay for Autonomous Detection of Toxins, manuscript attached, 5/515/2008).*
Witcombe et al. (Development of in vitro assays for the detection of botulinum toxins in foods, FEMS Immunology and Medical Microbiology 24 (1999) 319-323).*
Pappert et al. (Immunomagnetic nanoparticle-based sandwich chemiluminescence-ELISA for the enrichment and quantification of *E. coli*, Microchim Acta (Dec. 29, 2010) 168:1-8).*
Sumida et al. (Bicistronic DNA display for in vitro selection of Fab fragments, Nucleic Acids Research, 2009, vol. 37, No. 22, Sep. 29, 2009).*
Olsvick et al. (Magnetic Separation Techniques in Diagnostic Microbiology, Clinical Microbiology Reviews, Jan. 1994, p. 43-54).*
Yan et al. (Nonprotein Based Enrichment Method to Analyze Peptide Cross-Linking in Protein Complexes, Anal Chem. Sep. 1, 2009; 81(17): 7149-59).*
Nielsen et al. (Multiplexed sandwich assays in microarray format, Journal of Immunological Methods 290 (2004) 107-120).*
Moises et al. (Toxin immunosensors and sensor arrays for food quality control, Bioanal Rev (Nov. 26, 2009) 1:73-104).*
Cammann (Sensors and analytical chemistry, Phys. Chem. Chem. Phys., 2003, 5, 5159-5168), Dworetzky (US 2002/0040000, published Apr. 4, 2002).*
Invitrogen-Dynal (Isolate almost any cell type from any species with Secondary Coated Dynabeads, attached, 2005).*
Iarke et al. (Immunomagnetic Cell Separation, in Methods in Molecular Medicine, vol. 58: Metastasis Research Protocols, vol. 2: Cell Behavior In Vitro and In Vivo, 2001).*
Casals et al. (Evaluation of a new ultrasensitive assay for cardiac troponin I, Clinical Biochemistry 40 (2007) 1406-1413).*
Siemens (Early Detection of Diseases—Biomarkers, Pictures of the Future Fall 2008, attached).*
Nam et al. (Nanoparticle-Based Bio-Bar Codes for the Ultrasensitive Detection of Proteins, Science 301, 1884 (2003)).*
Nilsson et al. (Antigenic determinants of prostate-specific antigen (PSA) and development of assays specific for different forms of PSA, British Journal of Cancer (1997) 75(6), 789-797).*
FujireBio (Antibodies and Antigens—Total PSA, attached, Apr. 20, 2008).*

(Continued)

*Primary Examiner* — Aaron Priest

(57) ABSTRACT

The present invention is related to a method for detection of a biological target in an affinity assay, the method comprising the steps of providing a biological sample volume containing the biological target, adding a first capturing moiety to the biological sample volume comprising the biological target, wherein the first capturing moiety is adhered to a particle, concentration of the captured biological target into an elution volume that is smaller than the biological sample volume in step a), cleavage of the first capturing moiety or the biological target from the particle and direct or indirect detection and/or quantification of the biological target in a sandwich or competitive affinity assay format, wherein the biological target is associated with at least one capturing moiety, preferably at least two capturing moieties.

6 Claims, 10 Drawing Sheets

(56) References Cited

OTHER PUBLICATIONS

Park et al. (Useful Tools for Biomolecule Isolation, Detection, and Identification: Acylhydrazone-Based Cleavable Linkers, Chem Biol. Jul. 31, 2009;16(7):763-72).*

Von Schonfeldt (Magnetic Cell Sorting Is a Fast and Effective Method of Enriching Viable Spermatogonia from Djungarian Hamster, Mouse, and Marmoset Monkey Testes, Biol Reprod. Sep. 1999;61(3):582-9).*

Pappert, Gerhard et al "Immunomagnetic Nanoparticle-based Sandwich Chemiluminescence-ELISA for the Enrichment and Quantification of *E. coli*", Microchimica Acta; vol. 168, No. 1-2, Dec. 29, 2009, pp. 1-8.

Sabatte, Gwenola et al "Protein Biomarker Enrichment by Biomarker Antibody Complex Elution for Immunoassay Biosensing", Biosensors and Bioelectronics, vol. 29, 2011, pp. 18-22.

* cited by examiner

A

B

MULTI EPITOPE ASSAY

FIELD OF THE INVENTION

The invention relates to the field of affinity assays. In particular, the invention relates to a method for detection of a biological target in an affinity assay as well as a detection arrangement for a biological target.

BACKGROUND OF THE INVENTION

An affinity assay is a biochemical test that measures the presence or concentration of a substance, the analyte, in solutions that frequently contain a complex mixture of substances, e.g., biological liquids such as blood, saliva, serum or urine. Such assays are based on the ability of a given molecule or a specific part of the molecule, e.g., an antibody to bind with high specificity to one or a very limited group of other molecules. The specificity of the assay depends on the degree to which the analyte is able to bind to its specific binding partner to the exclusion of all other substances in the sample to be analyzed.

In addition to the need for specificity, a binding partner must be selected that has a sufficiently high affinity for the analyte to generate an accurate and reproducible measurement, i.e., a measurable signal. Historically, this was accomplished by measuring a change in some physical characteristic such as light scattering or changes in a refractive index. With modern instrumentation, such methods are again becoming increasingly popular. Nevertheless, most immunoassays today depend on the use of an analytical reagent for binding to the analyte, which is associated with a detectable label. A large variety of labels have been demonstrated including radioactive elements used in radioimmunoassays; enzymes; fluorescent, phosphorescent, and chemiluminescent dyes; latex and magnetic particles; dye crystallites, gold, silver, and selenium colloidal particles; metal chelates; coenzymes; electroactive groups; oligonucleotides, stable radicals, polymers and others. Such labels serve for detection and quantitation of binding events either after separating free and bound labeled reagents or by designing the system in such a way that a binding event affects a change in the signal produced by the label.

An affinity assay usually probes the interaction of peptides, proteins, oligonucleotides, oligosaccharides or small molecules, such as aptamers, with immobilized binding partners. Typical binding partners include proteins, which can be receptors, enzymes or antibodies, but also polypeptides and polyamino acids (e.g., a poly-His tag for nickel binding sites, poly-lysine for amide or Schiff base linkages, poly-cysteine for thioether linkages). For example, streptavidin based immobilization schemes have widely been employed to attach a biotinylated biological element to an assay surface.

Affinity assays can be further classified for example, as competitive and non-competitive assays. In a competitive affinity assay, the analyte in the biological sample competes with a labeled analyte analogue to bind with its partner. The amount of labeled analyte analogue bound to the partner is then measured. In this method, the response signal will be inversely related to the concentration of the analyte in the biological sample. This is because the greater the response signal, the less analyte was available in the biological sample to compete with the labeled analyte analogue.

In non-competitive affinity assays, also referred to as the "sandwich assays", an analyte in the biological sample is bound to its partner, then a labeled reagent is bound to the analyte. The amount of labeled reagent on the site is then measured. Unlike the competitive method, the results of the non-competitive method, i.e., the sandwich assay, will be directly proportional to the concentration of the analyte in the biological sample. This is because labeled reagent will not bind if the analyte is not present in the biological sample.

Affinity assays and, in particular, immunoassays are widely used as diagnostic tools in bacterial, viral, endocrine and parasitic diseases, as well as to detect drugs of abuse and chronic disease states, one example being heart disease which can lead to a heart attack.

Various techniques such as radioimmunoassay, immunoperoxidase, and ELISA are presently used for affinity assays and especially immunoassays. However, radioimmunoassays have the disadvantage of requiring the use of dangerous and environmentally unsound reagents.

Furthermore, apart from the specificity, as mentioned above, the sensitivity is of critical importance to the assay performance. An assay's sensitivity can be defined by the ratio of the specific signal generated by the binding event compared to the background noise of the system.

Factors decreasing the signal to noise ratio (SNR) include non-specific binding of reagents such as an antibody to various components of the assay. Moreover, the activity of some endogenous components of the assay matrix that react with the reagents of the assay, e.g., an enzyme substrate tends to yield a "false" reaction product that interferes with the accurate detection of the "true" product formed by a labeled complex, e.g., a labeled antibody-antigen complex.

Typically, additives such as blocking reagents are added to the assay matrix to lower assay noise and reduce the false positive signals.

SUMMARY OF THE INVENTION

It is an object of the invention to provide an affinity assay with a higher signal to noise ratio compared to affinity assays known from the art.

It is yet another object of the present invention to provide such an affinity assay that is suitable for a wide range of analytes.

In particular, it is an object of the invention to provide an affinity assay that is suited for integration into point-of-care, or bench-top, devices and miniaturization.

It is another object of the present invention to provide a fast and reliable affinity assay giving a minimum of false-positive results.

These objects are achieved by the method for detection of a biological target in a biological sample by an affinity assay as set forth in the independent claims. The dependent claims indicate preferred embodiments. In this context it is noteworthy to mention that all ranges given in the following description are to be understood that they include the values defining these ranges.

BRIEF DESCRIPTION OF THE DRAWINGS

These and other aspects of the invention will be apparent from and elucidated with reference to the embodiments described hereinafter.

DETAILED DESCRIPTION OF EMBODIMENTS

Figure 1:
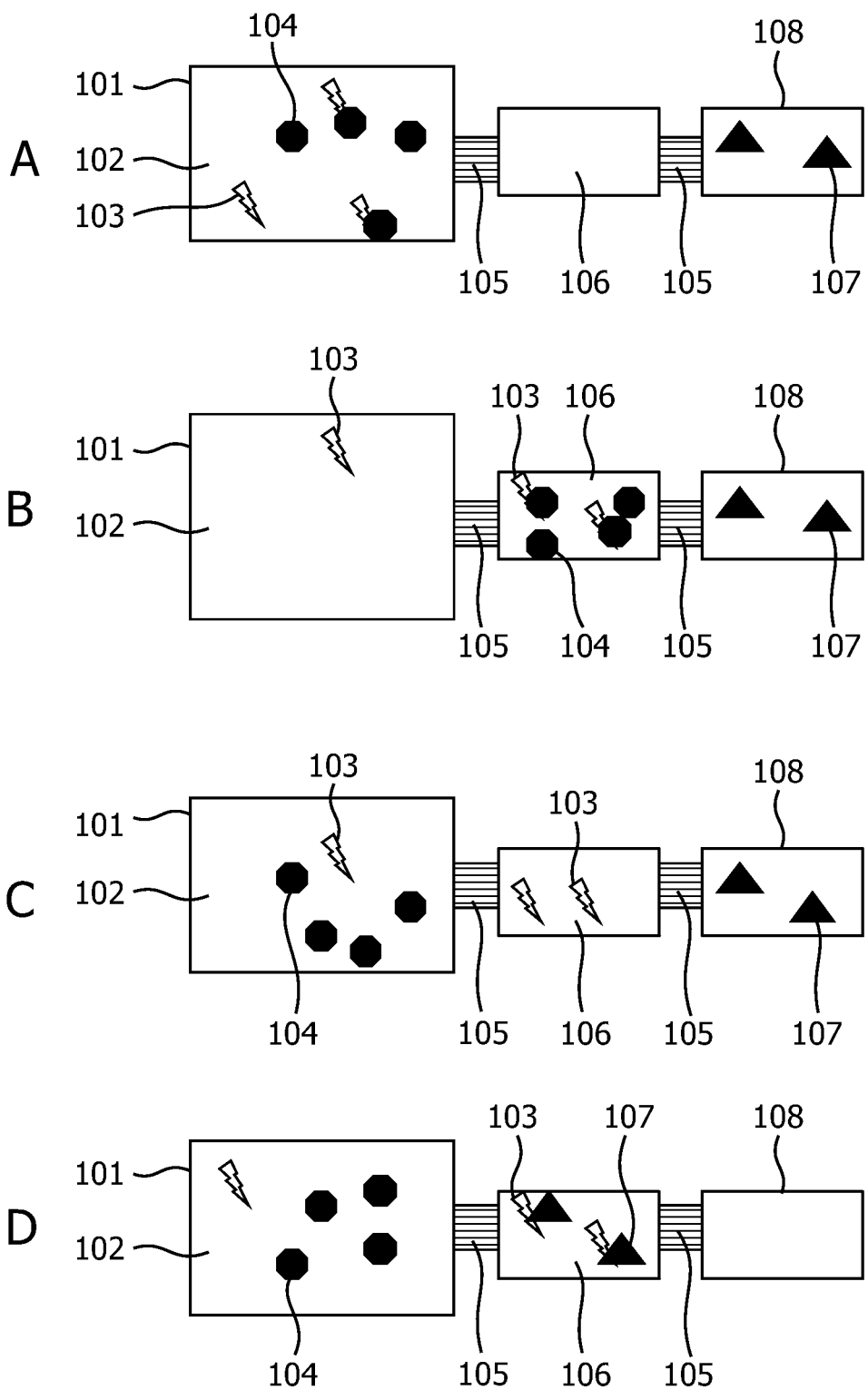
FIG. 1 shows in a schematic fashion one example of a concentration of the captured biological target into an elution volume that is smaller than the biological sample volume according to the invention as well as further optional steps for detection and/or quantification.

According to the invention a method for detection of a biological target in a biological sample by an affinity assay, comprising the steps of
a) providing a biological sample volume containing the biological target,
b) adding a first capturing moiety to the biological sample volume comprising the biological target, wherein the first capturing moiety is adhered to a particle,
c) concentrating the captured biological target into an elution volume that is smaller than the biological sample volume in step a),
d) cleaving the first capturing moiety or the biological target from the particle,
e) direct or indirect detecting and/or quantifying of the biological target in a sandwich or competitive affinity assay format, wherein the biological target is associated with at least one capturing moiety, preferably at least two capturing moieties.

This affinity assay has the advantage that the biological target is concentrated and factors that could interfere with the detection are removed thus leading to increased specific and decreased nonspecific binding and hence to a greatly increased signal to noise ratio and higher sensitivity of the assay.

Specifically, it is beneficial when the binding of the biological target to the first capturing moiety and the detection and/or quantification of the biological target are uncoupled. Thus the amount of first capturing moieties, with adhered particles, can be large in order to capture as many biological targets as possible, but the first capturing moieties, with adhered particles, do not interfere with the detection and/or quantification of the biological target. For example, if the first capturing moieties, with large magnetic particles adhered to them, are used to capture the biological target in a large volume, e.g., the biological sample, these are easier to actuate than smaller particles. Hence, it is easier to collect these larger particles from a large volume, the biological sample, and transfer them and the bound biological target to a smaller volume, the elution volume.

As used herein the term "biological target" refers to a substance of biological origin to be detected. Non limiting examples of the biological target are proteins, peptides, antibodies, toxic agents, lipids, amino acids, amines, messenger or small molecules, carbohydrates, cellular components, viruses, components of the extracellular matrix, cells, cell fragments, nucleic acids, haptens and/or drugs.

As used herein the term "affinity assay" refers to a biochemical test that measures the presence or concentration of the biological target based on the ability of a capturing moiety to bind with high specificity to the biological target and optionally to one or a very limited group of other molecules.

As used herein the term "biological sample volume" refers to the volume or part of the volume in which the biological target is initially provided.

As used herein the term "capturing moiety" refers to a binding element, e.g., a moiety which contains a complementarity determining region which binds selectively to an epitope of the biological target and which may bind to at least one other entity, such as the particle, and which may have a reagent associated with it.

In a preferred embodiment, the capturing moiety is an antibody, for example animal, human, human chimeric, and humanized antibodies, and fragments thereof, such as a Fab fragments, and the like, or an aptamer, or a nucleic acid or a polypeptide or anything that comprises a binding site.

As used herein the term "binding element" refers to a site where another element can bind or associate. In a preferred embodiment of the invention, the binding site is an epitope, i.e., an antigenic determinant, i.e. the part of an antigen that is recognized by the immune system, specifically by antibodies, B cells, or T cells.

Aptamers are oligonucleic acid or peptide molecules that bind to a specific target molecule. Aptamers are usually created by selecting them from a large random sequence pool, but natural aptamers also exist in riboswitches.

As used herein the term "particle" refers to a structure, e.g., a bead capable of supporting the adhering of a capturing moiety. The particle can be manufactured from agarose, polystyrene, latex, polyvinyl alcohol, silica. In a preferred embodiment the particle has a diameter between 5 μm and 0.1 μm, more preferred between 1 μm and 0.3 μm, i.e., ≥0.3, 0.4, 0.5, 0.6, 0.7, 0.8, 0.9 and/or ≤1 μm.

As used herein the term "cleavage" refers to the separation of a capturing moiety from the particle or to the separation of the biological target from the capturing moiety.

As used herein the term "adhere to" refers to the fact that the capturing moiety is adhered to the particle via a linker.

As used herein the term "linker" refers to a structure that allows for the separation of the first capturing moiety from the particle. The linker can be located on the first capturing moiety and/or in the particle. This could for instance be the case if pH-induced cleavage is to be employed. Alternatively, the linker can be a separate structure that is coupled to both the capturing moiety and/or in the particle.

Figure 5:
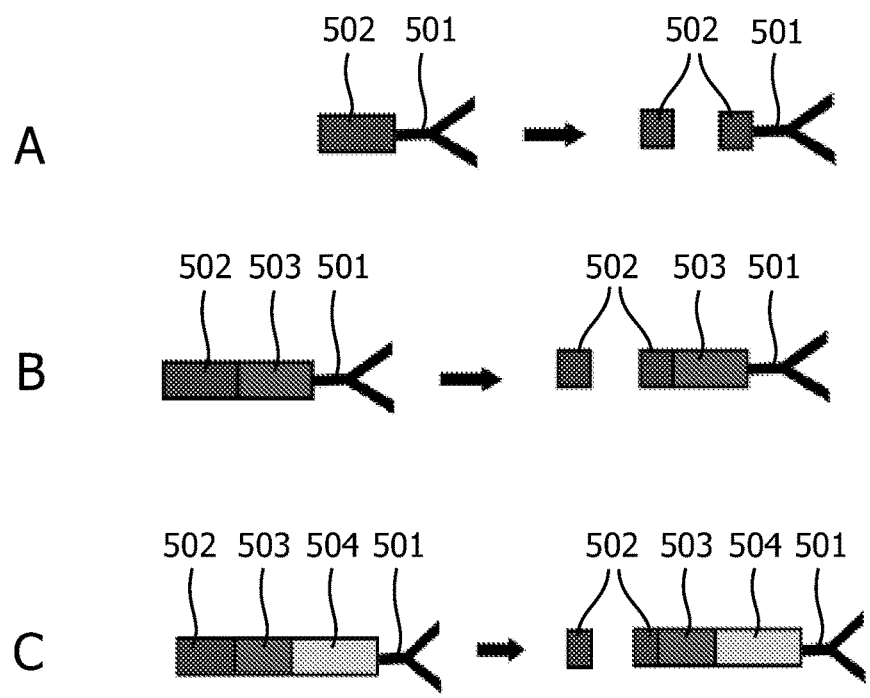
FIG. 5 shows some examples of the modular design of suitable linkers.

The linkers can be built using a modular design; a few examples are given in FIG. 5. In principle any coupling (bio)chemistry can be used (carboxyl, amine, sulfhydride, maleimide, etc.), preferably different from each other. Furthermore, the linker should contain a cleavable entity. Examples of cleavable entities and methods of cleaving include, but are not limited to:

Peptides that can be cleaved by a protease (preferably a specific amino acid sequence) and/or, Nucleic acid sequences that can be cleaved by a nuclease (preferably a specific sequence/nuclease) and/or, Photocleavable elements and/or, Temperature-induced cleavage and/or, Chemically induced cleavage (e.g. reduction of S—S bond) and/or, pH-induced cleavage.

An example for a linker is a fragment of synthetic DNA containing a restriction site, but many different options for linkers are available.

As used herein the term "associated with" refers to a physical association.

As used herein the term "direct detection and/or quantification" implies that the biological target itself is detected and/or quantified.

As used herein the term "indirect detection and/or quantification" means that a competitive affinity assay is used in which, not the biological target itself is detected and/or quantified, but an entity that is competing with the biological target for the at least one capturing moiety of step e) for example an analogue to the biological target.

In a preferred embodiment the at least one capturing moiety in step e) is part of a detection surface.

As used herein the term "detection surface" refers to a surface capable of binding the biological target as well as enabling detection. The detection surface may be biological, non-biological, organic, inorganic or a combination thereof, and may be in the form of particles, strands, precipitates, gels, sheets, tubings, spheres, containers, capillaries, pads, slices, films, plates, slides, etc., having any convenient shape, including disc, sphere, circle, etc. for the purposes of the present invention as long as it allows detection of the bound biological target.

In such a setting it is especially preferred that the at least one capturing moiety in step e) comprises a biochemical molecule or a structure, constructed in such a way that it permits binding to a support as well as to the biological target. Examples for such a biochemical molecule or a structure are nucleic acids, preferably DNA oligonucleotides of up to 200 bases, as well as proteins and haptens, like antibodies or lectins, which can bind molecular structures such as DNA sequences, antibodies, antigens, or enzymes.

The at least one capturing moiety in step e) can also comprise a strongly binding substance such as streptavidin.

As used herein the term "detection" refers to determining the physical presence of the biological target and/or quantitative detection of the biological target.

In a preferred embodiment, the affinity assay is an immunoassay, i.e., the assay utilizes an antibody to specifically bind an analyte, i.e., the biological target. This is advantageous for those biological targets for which a good choice of different antibodies with different binding sites is available, since antibody-antigen binding is usually highly specific and very sensitive.

In another preferred embodiment steps a) to d) are applied one or more times in sequence. This is advantageous since it allows for a higher enrichment and/or purification of the biological target in solution.

Moreover, it is preferred that the biological target is associated with at least two capturing moieties in step e) wherein one of the two capturing moieties is part of a detection surface and the other one enables detection on this surface. In other words, the biological target is bound directly to the detection surface.

This direct binding of the biological target to the capturing moiety of the detection surface has the advantage that no additional serial binding step is required for detection and/or quantification of the biological target.

In a further preferred embodiment of the method according to the invention in step e) the first capturing moiety or a second capturing moiety is associated with another capturing moiety.

Thus if the first capturing moiety was cleaved from the particle together the biological target, the first capturing moiety, or a part of it, can be used to bind to another capturing moiety. Preferably, the additional capturing moiety is part of the detection surface. In this way, the biological target is indirectly bound to the additional capturing moiety and hence to the detection surface, thereby enabling detection (see for example FIG. 3B).

As used herein the term "indirect binding" means that the biological target itself is not bound to the detection surface. Instead, a part of the first capturing moiety, e.g., a third entity or tag, is bound to the detection surface (see, for example, FIG. 3B and FIG. 3C).

Indirect binding is especially advantageous if the biological target only has one site where a capturing moiety can bind, as this site will already be occupied by the first capturing moiety at the time when recapturing of the biological target on the detection surface occurs.

Alternatively, regardless of whether the first capturing moiety was cleaved from the particle together with the biological target or not, a second capturing moiety could bind to the biological target and this second capturing moiety in turn can be used to bind to another capturing moiety. Thus again if the additional capturing moiety is part of a detection surface the biological target is indirectly bound to the additional capturing moiety and hence to the detection surface, thereby enabling detection (see, for example, FIG. 3C).

In a further preferred embodiment of the method according to the invention, the biological target is associated with a further capturing moiety in step e).

Thus in this preferred embodiment the biological target is associated with at least three capturing moieties. These could be, for example, the first capturing moiety—that was cleaved together with the biological target from the particle—as well as two additional capturing moieties one of which is part of a detection surface and the other one enables detection on this surface. In other words, the biological target is bound directly to the detection surface (see for example FIG. 3D).

This direct binding of the biological target to the capturing moiety of the detection surface has the advantage that no additional serial binding steps are required for detection and/or quantification of the biological target.

Moreover, the biological target could be associated with four capturing moieties, this could be the case if the first capturing moiety was cleaved together with the biological target from the particle. The second capturing moiety, possibly coming from a second round of concentrating the biological target, and also remaining attached to the biological target after cleavage, binds to a third capturing moiety, which is part of a detection surface, and the fourth capturing moiety attached to a particle, enables detection on this detection surface. The second moiety can bind to the third capturing moiety via a DNA-linker with an epitope that is recognized by the third capturing moiety.

This arrangement is, for example, advantageous if the binding between the capturing moiety of the detection surface, i.e., the third capturing moiety and the second capturing moiety is mediated via a strongly binding substance, such as the interaction of biotin and streptavidin.

In a further preferred embodiment of the method according to the invention a reagent is associated with at least one capturing moiety or in the case of a competitive affinity assay format with an analogue of the biological target in step e).

As used herein the term "reagent" refers to a substance that enables and/or facilitates the detection of the biological target in an affinity assay.

As used herein the term "analogue of the biological target" refers to a substance that competes with the biological target for the binding sites in a competitive affinity assay.

An affinity assay comprising this additional step is advantageous, because the reagent can be any one of a number of substances, which work with well-established detection systems known in the art. Thus, the actual detection reaction can be chosen from a wide variety of known methods regardless of the biological target assayed.

If the affinity assay contains this additional step it is beneficial if the linker contains a spacer element, since the distance between the detection surface and the reagent is increased which allows a better distinction between nonspecific and specific binding.

Preferably the reagent is selected from the group consisting of:
 radioisotopes and/or
 solid phases, such as a magnetic bead, or a latex bead, or a detection surface, and/or
 fluorescent, phosphorescent, and/or chemiluminescent dyes and/or,
 enzymes and/or enzyme substrates, and/or
 nucleic acid sequences, peptides, and/or
 colloid or nanoparticles and/or
 polymers or macromolecules, such as dendrimers, or liposomes.

In a preferred method according to the invention, the concentration of the captured biological target into a second volume that is smaller than the biological sample volume in step a) occurs via magnetic separation or gravitational forces.

Preferably, in the concentration step the biological sample volume is reduced by a ratio between 1:2 and 1:1000, i.e., by 1:2, 1:3, 1:4, 1:5, 1:6, 1:7, 1:8, 1:9, 1:10, 1:20, 1:30, 1:40, 1:50, 1:100, 1:200, 1:500 and/or 1:1000.

Moreover, the biological sample volume preferably has a volume between 1 µl and 5 ml, i.e. ≤1 µl, 2 µl, 3 µl, 4 µl, 5 µl, 6 µl, 7 µl, 8 µl, 9 µl, 10 µl, 11 µl, 12 µl, 13 µl, 14 µl, 15 µl, 16 µl, 17 µl, 18 µl, 19 µl, 20 µl, 21 µl, 22 µl, 23 µl, 24 µl, 25 µl, 26 µl, 27 µl, 28 µl, 29 µl, 30 µl, 50 µl, 100 µl, 300 µl, 500 µl, 1 ml, 3 ml and/or 5 ml.

The biological sample volume after the concentration step, here also referred to as the elution volume, can end up to be, e.g., 5 µL for enzymatic elution and 15 µL for photochemical elution.

Both methods available for concentrating the biological target in step a), magnetic separation or gravitational forces are techniques that are fast, reliable.

In an alternative embodiment, the reduction of the ratio of the biological sample volume to biological target occurs via filtration. In this case, the particle could be a His-tag, i.e., an amino acid motif that consists of at least five histidine (His) residues, and the filtration could be carried out using affinity media such as Ni Sepharose, NTA-agarose, His60 Ni, His-Pur resin, or Talon resin.

Preferably, the particle is a magnetic particle and/or a super-paramagnetic particle. This is beneficial since a magnetic particle and/or a super-paramagnetic particle has a high surface-to-volume ratio, and a magnetic particle enables reduction of the ratio of the biological sample volume to the biological target via magnetic separation.

For example, if the particle is a magnetic particle, the method according to the invention could proceed as follows: First, a biological sample volume containing the biological target is provided in a first chamber. Then, a first capturing moiety is added which is adhered to a magnetic particle. After sufficient binding occurs between the biological target and the first capturing moiety adhered to the magnetic particle, the capturing moiety with the biological target is transferred to a second, smaller chamber using magnetic forces, thereby reducing the ratio of the biological sample volume to the biological target. Subsequently, the first capturing moiety is cleaved from the magnetic particle and the magnetic particle is removed from the second, smaller chamber. Finally, recapturing of the biological target on a detection surface takes place, and detection and/or quantification of the biological target on the detection surface are carried out.

Using this approach, a high amount of magnetic particles can be used to isolate and concentrate the biological target within the biological sample volume, without interfering with subsequent detection steps.

In a further preferred method according to the invention, the cleavage of the first capturing moiety from the particle occurs via enzymatic, thermal and/or photochemical cleavage.

Each of the different cleavage methods, which can also be used in combination, in parallel or after each other, has its specific advantages. However, all of them can be used in combination with an affinity assay, since all of them cause minimal interferences and minimal contamination of the fluid. Alternative methods, e.g., cleavage via lowering the pH or chemical induced cleavage such as a reduction reaction, can strongly affect the state and conformation of the biological target and can change the chemical conditions of the solution and thereby strongly interfere in the subsequent affinity assay. Even though these last two approaches are both simple well-known ways of eluting an analyte from an antibody, they have the disadvantage of affecting the affinity assay for the biological target later on in the process.

Enzymatic cleavage for instance can be used with all targets and it is a mild process that can be used with biological targets that are proteins, as it does not typically denature them. Hence, the method according to the invention is especially advantageous for the concentration i.e. enrichment of proteins, which is usually very challenging to perform due to the sensibility of protein molecules to temperature and buffer formulation changes. Moreover enzymatic cleavage allows for a subsequent immunoassay. The advantage of using DNA is the performance of the assay can be enhanced by placing the restriction site away from where the antibody binds. The remaining DNA linker can be used to enhance the detection signal on the final assay.

Preferred enzymes for cleavage are DNase and EcoRI. For a preferred embodiment, DNAse showed a higher yield than EcoRI. Any specific nuclease enzyme can be used with minimal effect on the DNA sequence. Here, in the preferred embodiment, EcoRI was used to show that the system could be adaptable and also to show the versatility of the methods for nucleic acid detection.

Thermal cleavage has the advantage that the cleaving site has less specific requirements than with enzymatic cleavage, it is especially well suited for biological targets that can withstand high temperatures, e.g., small molecules. However, thermal cleavage can also be carried out on biological targets that are proteins if care is taken not to use temperatures that can denature them.

In the case of thermal cleavage the step of cleavage of the first capturing moiety from the particle can be replaced by cleavage of the biological target from the first capturing moiety. However, of course it is also possible to build a thermal cleavage site into a linker and/or the first capturing moiety itself.

Photochemical cleavage is beneficial since no additional substrates, such as enzymes for enzymatic cleavage, need to be added. Photochemical cleavage showed also some advantages in terms of integration of this assay into a compact device.

However, with this form of cleavage the assay needs to take place in a surrounding, e.g., a cartridge, that permits for the penetration of light.

Furthermore, it is preferred that the detection and/or quantification method is selected from the group consisting of:
- optical detection, e.g. fluorescence, phosphorescence, chemiluminescence, absorption, scattering, imaging, evanescent field techniques, frustrated total internal reflection, surface plasmon resonance, Raman, spectroscopy, and/or,
- enzyme reaction, and/or,
- nucleic-acid amplification techniques, e.g. immuno-PCR, rolling circle amplification, and/or,
- magnetic detection, e.g. by magnetoresistance, Hall effect, coils and/or,
- sonic detection, e.g. surface acoustic wave, bulk acoustic wave, cantilever, quartz crystal, and/or,
- electrical detection, e.g. conduction, impedance, amperometric, redox cycling, charge, and/or
- optomagnetic detection.

One optical detection technique is frustrated total internal reflection, (FTIR). Illuminated at the correct angle, light hitting the underside of a sensor's active surface is normally reflected without any loss in intensity, this is total internal reflection. However, when nanoparticles are bound to the opposite side of the surface they scatter and absorb the light, reducing the intensity of the reflected beam. These intensity variations in the reflected beam, which correspond to the number of bound nanoparticles, are detected by a sensor, e.g., a CMOS image sensor similar to that used in a digital camera. This is FTIR.

In the state of the art, various suitable enzyme reactions such as horseradish peroxidase are well known.

Immuno-PCR is an antigen detection system, in which a specific DNA molecule is used as the marker and PCR is employed to detect this marker.

If the reagent is a magnetic particle, the preferred method of detection is FTIR, as it is reliable, fast and can work in a small volume.

In a preferred embodiment of the method according to the invention, the cleavage is enzymatic, the reagent is a magnetic bead and the biological target is associated with a further capturing moiety.

In a further preferred embodiment the binding of the biological target to the first capturing moiety, a second capturing moiety and a third capturing moiety all take place via binding sites on the biological target.

In such a case, three binding sites on the biological target are occupied by the first capturing moiety, the second capturing moiety associated with a reagent and a third capturing moiety, which preferably is part of the detection surface.

The inventors of the present invention have surprisingly found that even though two binding sites on the biological target are already occupied the target can still bind directly via a third binding site to the detection surface. In other words, the already bound elements do not sterically hinder detection of the biological target molecule, even though in the case of a magnetic bead as the reagent, the second capturing moiety reagent complex is very large.

In a further preferred embodiment, the binding of the biological target to the first capturing moiety, a second capturing moiety and a third capturing moiety all take place via binding to epitopes, i.e., antigenic determinants of the biological target.

This "three-epitope-assay" is advantageous as it has high specificity due to the binding to three antigenic determinants of the biological target. Moreover, due to the enzymatic cleavage of the first capturing moiety from the particle the biological target is sterically highly accessible for the second capturing moiety associated with the reagent and the direct binding to the detection surface.

In an alternative embodiment, a detection arrangement for a biological target is provided comprising a first, a second and a third capturing moiety, wherein a reagent is associated with the second and/or the third capturing moiety and the biological target is bound directly to all three capturing moieties thereby enabling detection.

In a preferred embodiment of this detection arrangement, the biological target is bound to all capturing moieties via epitopes.

In a further alternative embodiment, a capturing moiety is provided, comprising
a) a first entity for attachment to a particle,
b) a second entity for cleavage of the attachment to a particle, and
c) a third entity for attachment to a detection surface.

Preferably the capturing moiety according to claim 1 is used as a first capturing moiety in a method according to anyone of the claims 1 to 6.

Thus, when using this embodiment the first capturing moiety is bound to the biological target and is cleaved together with the biological target from the particle.

Preferably the detection surface comprises a further capturing moiety.

In contrast to the above-described three-epitope assay, the binding to the detection surface is indirect because the third entity binds to the detection surface and not the biological target.

In this case, it is beneficial if the linker contains a spacer, since this increases the binding area of the third entity on the detection surface. Particularly a spacer increases the area of finding a binding place on the detection surface, as more orientations or space in which the third entity can successfully bind.

In general, the first capturing reaction occurring during step b) of the method according to the invention can be investigated as a function of time and the concentration of particles. The interaction between the first capturing moiety and the biological target occurring during step b) can be simulated as a first order rate expression and after rearrangement; the capture efficiency ($\varepsilon_{capt}$) is given by:

$$\varepsilon_{capt} = 1 - e^{\left(-\frac{t_{capt}}{\tau}\right)} \text{ with } \tau = \frac{1}{k_{on}[Ab]} \quad (1)$$

where, $tc_{apt}$ is the experimental incubation time for step b) of the method according to the invention, T the estimated capture constant, $k_{on}$ is the association rate constant in $M^{-1} \cdot s^{-1}$ and [Ab] is the concentration of first capturing moieties, for example antibodies, on the particles (M). τ is directly linked to the concentration of particles. In this capture step, the first capturing moieties concentration is proportionality to the amount of particles in the biological sample volume. When $t_{capt} \gg \tau$, $\epsilon_{capt}$ approaches 100%. When $t_{capt} \ll \tau$, then $\epsilon_{capt}$ is low and can be approximated by $t_{capt}$ over, τ which is proportional to the amount of particles in the biological sample volume.

Figure 11:
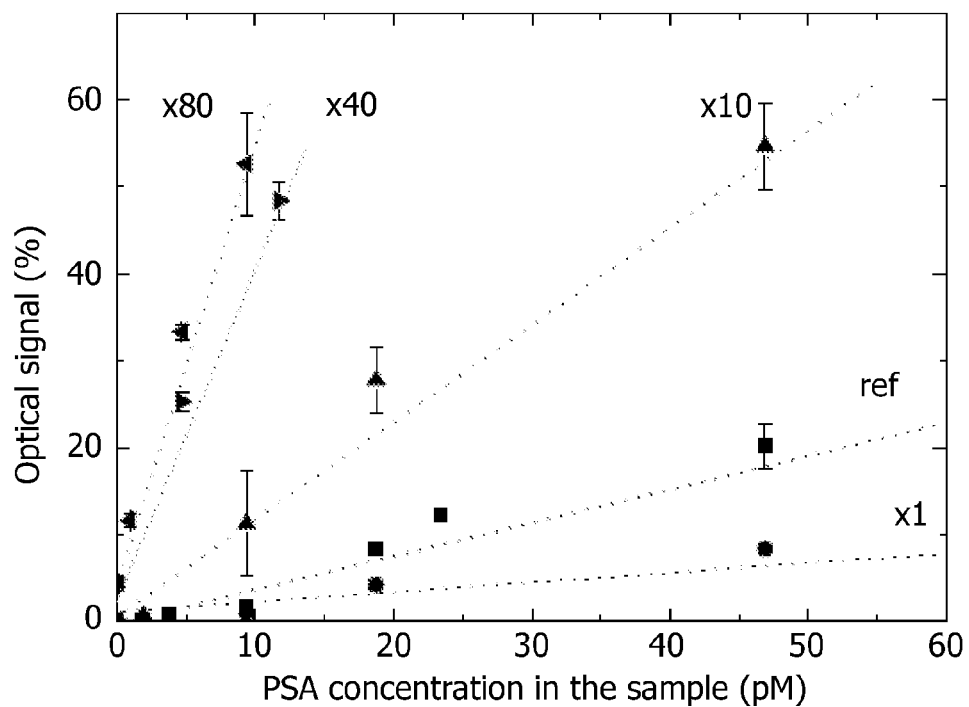
FIG. 11 shows an assessment of step c), i.e. of the concentration of a biological target for various volumetric enrichment factors.

Moreover as shown for example in FIG. 11, the enrichment factor (4) can be calculated. However, the enrichment efficiency is not linear to the volume ratio. For a thirty minute method, for a 1:1 volume, with a small amount of particles, the efficiency ξ of the whole method was determined at 0.29 and the enrichment gained for a 80:1 volume is about a factor 14.9. This could be understood by decoupling the method into the steps of capture, concentration and elution. The enrichment efficiency (4) is given by:

$$\xi = \varepsilon_{capt} \cdot \varepsilon_{conc} \varepsilon_{el} = \varepsilon_{capt} \cdot \frac{V_S}{V_{el}} \cdot \varepsilon_{el} \quad (2)$$

where (ξ) is the enrichment efficiency, $\epsilon_{capt}$, the capture efficiency, which is comprised between 0 and 1, $\epsilon_{conc}$, the concentration efficiency, which the ratio of the biological sample volume and the elution volume ($V_S/V_{el}$), which is superior than 1 if an enrichment is required, $\epsilon_{el}$, the elution efficiency, which is comprised between 0 and 1. The total efficiency, or the enrichment efficiency, is independent of the biological target concentration.

DISCUSSION OF THE FIGURES

Additional details, features, characteristics and advantages of the object of the invention are disclosed in the sub claims, the figures and the following description of the respective figures and examples, which—in an exemplary fashion—show several embodiments and examples of materials according to the invention. In the drawings:

FIG. 1 shows in a schematic fashion one example of a concentration of the captured biological target into an elution volume that is smaller than the biological sample volume, as well as further optional steps for detection and/or quantification. In this example, a first container 101 contains the biological sample volume 102, comprising biological targets 103 and first capturing moieties adhered to particles 104, in this case, magnetic beads. Moreover, the first container 101 stands in fluid communication with a second container 106, which is smaller than the first container, through a connection 105 and the second container 106 stands in fluid communication with a third container 108 through another connection 105. The third container 108 contains second capture moieties, associated with reagents 107.

FIG. 1A shows that some of the biological targets 103 have bound to the first capturing moieties adhered to magnetic beads 104. In the next step, in FIG. 1B, the first capturing moieties adhered to magnetic beads 104 have been transferred to the second container 106 using magnetic force. Thus also most of the biological targets 103 are now present in the second container 106 and consequently in a smaller elution volume. Hence a concentration of the captured biological target into an elution volume that is smaller than the biological sample volume has occurred.

In FIG. 1C the biological targets have been cleaved from the first capturing moieties adhered to magnetic beads 104, and the first capturing moieties adhered to magnetic beads 104 have been transferred back into the first container 101 using magnetic force.

In FIG. 1D the second capture moieties, associated with reagents 107, have been transferred from the third container 108 to the second container 106 via the connection 105 and the second capture moieties have recaptured the biological targets 103.

Using this approach, a high amount of first capturing moieties adhered to magnetic beads 104 (high bead concentration) can be used to capture the biological targets 103 whereas a smaller amount of the second capture moieties, associated with reagents 107, can be used for detection.

The concentration of the captured biological target into an elution volume that is smaller than the biological sample volume, as shown in this example, leads to a remarkable increase in signal to noise ratio which can be even further enhanced by the opportunity to exchange the solution of the biological sample volume for a different solution, for example, stored in the second container, which comprises less factors that could disturb detection.

Figure 2:
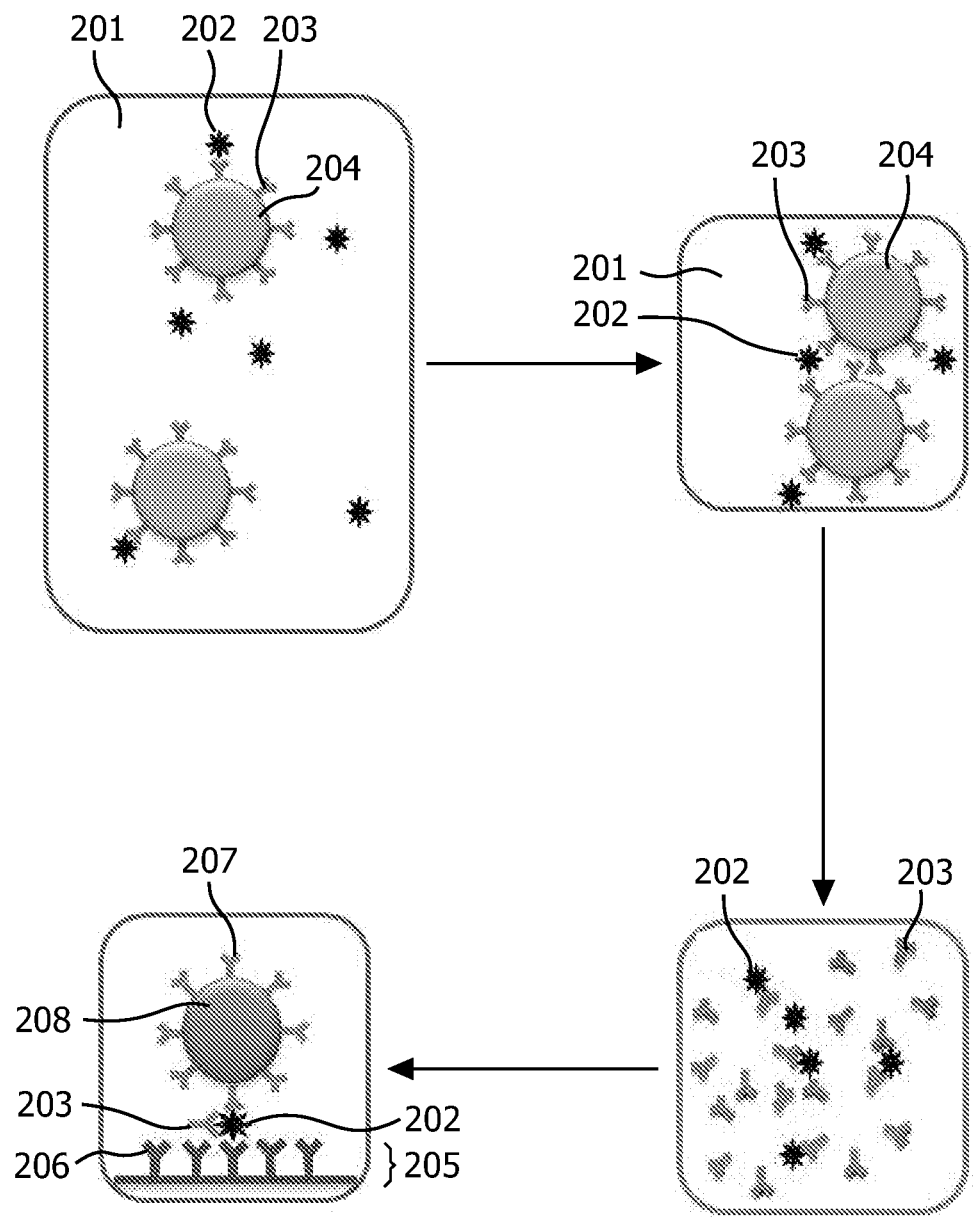
FIG. 2 shows in a schematic fashion one example of a method for detection of a biological target in an affinity assay according to the invention.

FIG. 2 shows in a schematic fashion one example of a method for detection of a biological target in an affinity assay according to the invention. After providing a biological sample volume 201 containing the biological target 202, a first capturing moiety 203, here an antibody to an epitope on the biological target, which is adhered via a DNA-linker 209 to a particle 204, in this FIG. 2, a streptavidin magnetic particle, is added. In the next step, a concentration of the captured biological target 202 into an elution volume that is smaller than the biological sample volume 201 occurs. This concentration of the biological target from a larger volume to a smaller volume occurs via transferring the magnetic particle 204 and hence the first capturing moiety 203 with any bound biological target to the smaller volume by magnetic force. Then the first capture moiety 203 is cleaved from the magnetic particle 204. In this example this occurs via treatment with the enzyme DNase, which cleaves the DNA-linker 209 at a predetermined position, thereby releasing the antibody-biological target complex and the unbound antibodies respectively from the magnetic particles 204. In the next step the biological target 202 is recaptured on a detection surface 205 comprising a third capture moiety 206, here antibodies, that bind the biological target 202. Moreover, a second capture moiety 207, which has a reagent 208, here a magnetic bead, associated with it, also binds the biological target 202. Thus, the formed complex is a three-epitope complex, which can be detected by FTIR on a Magnotech device. This device has the advantage that unbound or weakly bound magnetic beads are removed magnetically from the surface and thus can not interfere with detection. Step e) of the method according to the invention proceeds for example under switched actuation for four minutes. Instead of direct binding of the biological target at the detection surface it is also possible to use indirect binding, where a part of the first capturing moiety is bound to the detection surface. The part binding to the detection surface could be, for instance the remainder, the "tag", of the DNA-linker 209 cut to release the first capturing moiety from the particle. If this approach is chosen, the assay is termed a "tag-assay".

Figure 3:
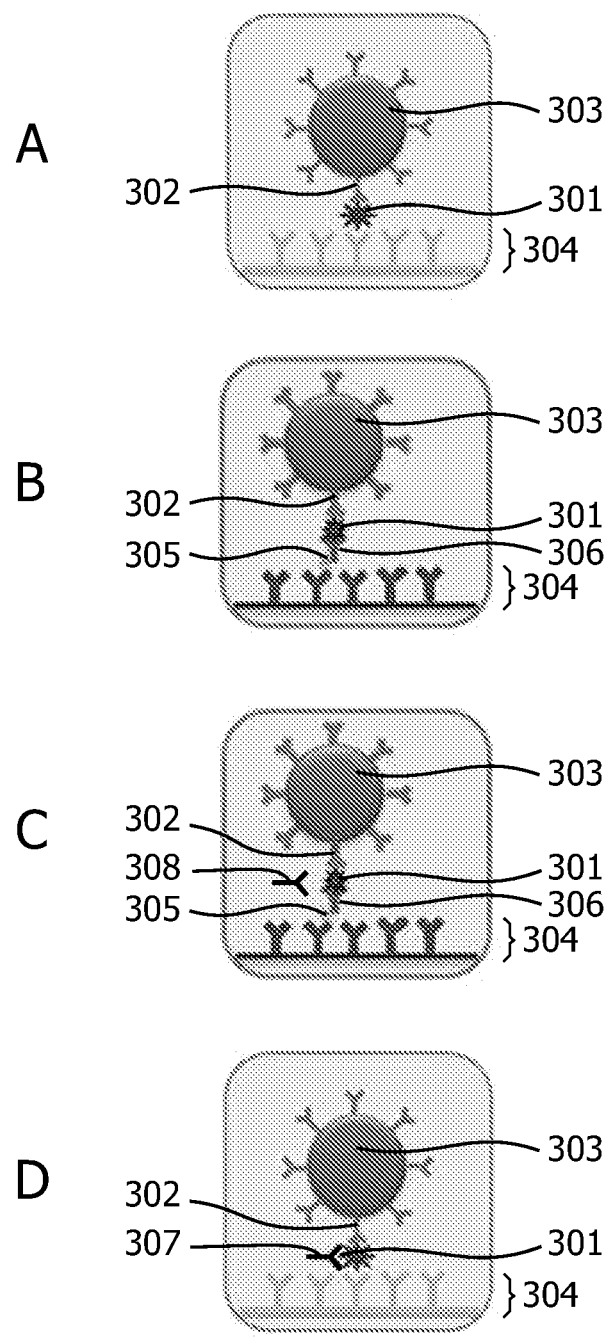
FIG. 3 shows another aspect of how the present invention achieves the object of increasing the signal to noise ratio.

FIG. 3 shows another aspect of how the present invention achieves the object of minimizing the signal to noise ratio. Shown in FIG. 3A is the end point, i.e., the detection of a signal in a conventional sandwich assay, where the biological target 301, is bound to a capturing moiety 302, which is associated with a reagent 303, here a magnetic particle, and a detection surface 304.

FIG. 3B shows the end point, i.e., the detection in a "tag-assay", where the biological target 301, is bound to a capturing moiety 302, which is associated with a reagent 303, here a magnetic particle, and a first capturing moiety 306, which comprises a further entity 305, a tag. The tag 305 then binds the detection surface 304.

FIG. 3C shows the end point, i.e., the detection in another "tag-assay", where the biological target 301, is bound to a first capturing moiety 308, which played a role in the concentration of the captured biological target into an elution volume that is smaller than the biological sample volume but does not play a role in detection and or/quantification of the biological target. For this event, i.e., the detection and or/quantification step, a second capturing moiety 302, which is associated with a reagent 303, here a magnetic particle, and another capturing moiety 306, which comprises a further entity 305, a tag are used. The tag 305 binds the detection surface 304. Thus, as the detection surface also comprises capturing moieties the assay comprises four different capturing moieties.

FIG. 3D shows the end point, i.e., the detection in the "three-epitope assay" as depicted in the last picture of FIG. 2 above. The biological target 301, is bound to a capturing moiety 302, which is associated with a reagent 303, here a magnetic particle. The biological target is also bound to a first capturing moiety 307 and the detection surface 304.

The tag-assay and the three-epitope assay are advantageous compared to the conventional sandwich assay since they allow for a reduction of the ratio of the biological sample volume to biological target that leads to a remarkable increase in the signal to noise ratio. Moreover, in both, the tag-assay and the three-epitope assay, the biological target can be purified through cleavage into a clean solution. In addition, in both assays, the problem of irreversible magnetic particle aggregation in a sample matrix can be avoided when using magnetic particles and both assays allow for the use of a strong binding agent, such as biotin, to increase assay reaction rates.

Figure 4:
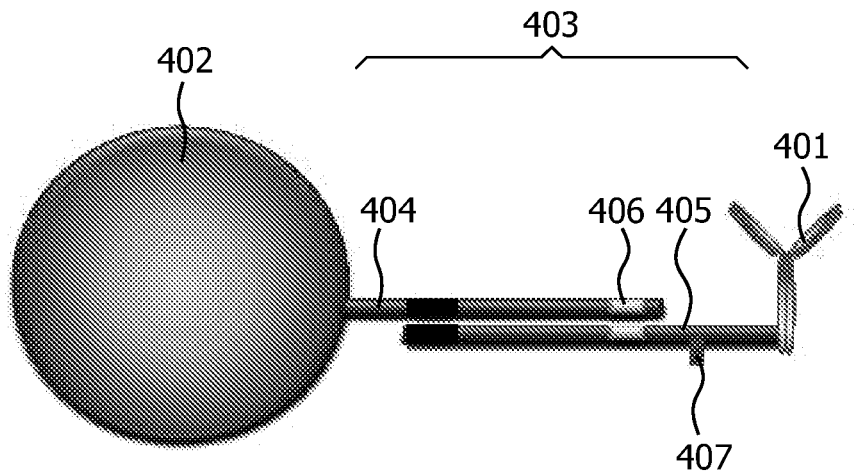
FIG. 4 shows examples of the organization of the first capturing moieties.
Figure 4:
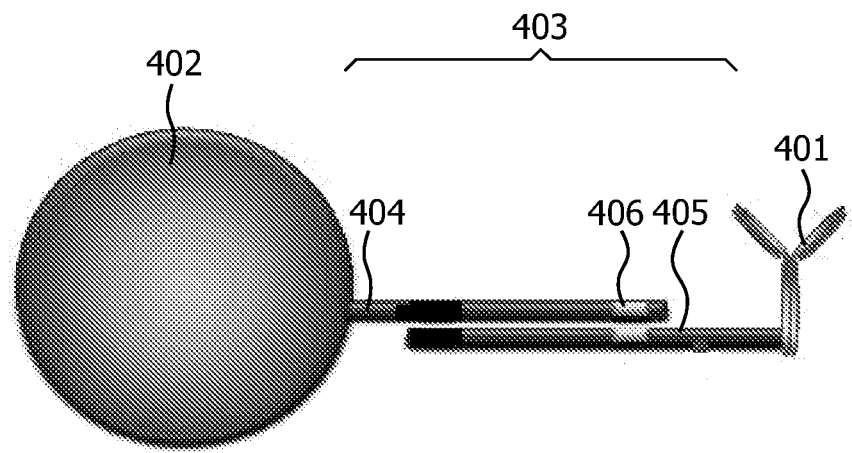

FIG. 4 shows examples of the organization of the first capturing moieties. FIG. 4A shows an example of a first capturing moiety 401 adhered to a particle 402. In this example the capturing moiety 401 is adhered to the particle 402 via a linker 403 comprising a first part 404 (i.e. a first entity), which is attached to the particle 402, and a second part 405, which is attached to the first capturing moiety 401. The linker 403 comprises a first predetermined position 406 (i.e. a second entity) at which the first capture moiety 401 can be cleaved from the particle 402 and a second predetermined position or area 407 (i.e. a third entity), which can bind to a detection surface (not shown). Thus this organization of a first capturing moiety 401 adhered to a particle 402 can be employed when performing a tag-assay.

FIG. 4B shows an example of a first capturing moiety 401 adhered to a particle 402. In this example the capturing moiety 401 is adhered to the particle 402 via a linker 403 comprising a first part 404 (i.e. a first entity), which is attached to the particle 402, and a second part 405 (i.e. a second entity), which is attached to the first capturing moiety 401. The linker 403 comprises a first predetermined position 406 at which the first capture moiety 401 can be cleaved from the particle 402. In contrast to the structure of FIG. 4A here no second predetermined position or area, which can bind to a detection surface is required. Thus this organization of a first capturing moiety 401 adhered to a particle 402 can be employed when performing a three-epitope assay.

FIGS. 4A and 4B can either be used for DNAse elution with the three-epitope assay recapture. Preferably, the design shown in FIG. 4A can be used for a tag assay as defined previously; FIG. 4B can preferably be used for recapture using the complementary single strand of DNA only.

FIG. 5 shows some examples of the modular design of suitable linkers. FIG. 5A shows a schematic example of a capturing moiety 501 comprising a linker 502 that can be cleaved into two parts.

FIG. 5B shows a schematic example of a capturing moiety 501 comprising a linker 502, which can be cleaved into two parts and a strong binding agent 503, in this case biotin.

FIG. 5C shows a schematic example of a capturing moiety 501 comprising a linker 502 that can be cleaved into two parts, a strong binding agent 503, here biotin, and a spacer 504. The use of biotin has the advantage that any particle can be adhered to the first capturing mioety as long as it comprises streptavidin or avidin.

Figure 6:
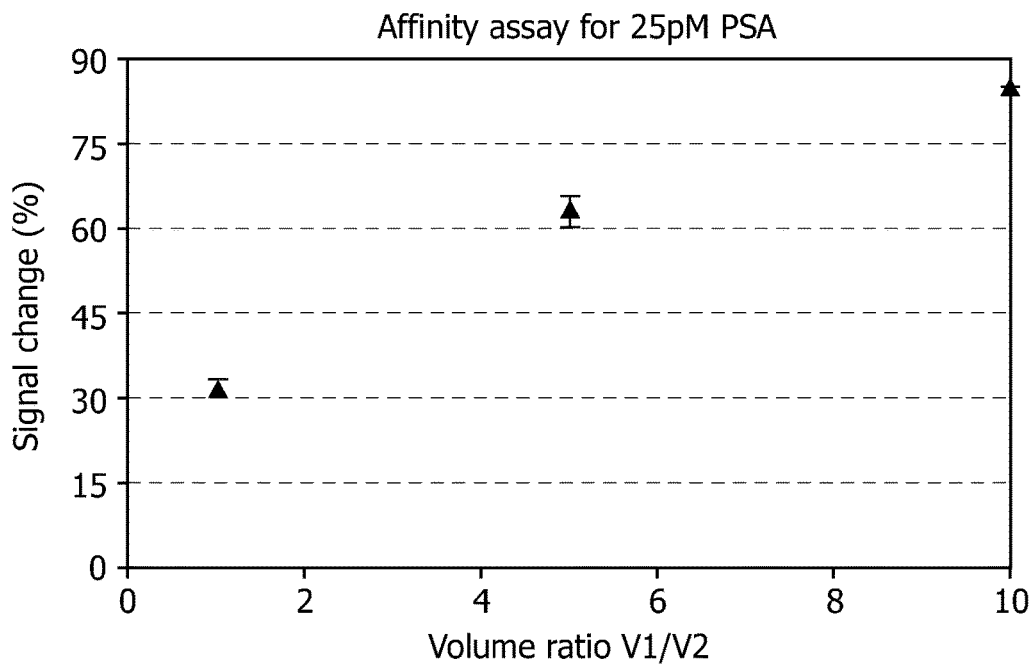
FIG. 6 shows the proof-of-concept of the three-epitope affinity assay with enrichment.

FIG. 6 shows the proof-of-concept of the three-epitope affinity assay described in FIG. 3 above. The employed biological target was PSA at 25 pM, the sample volume was 5 µl, the first capturing moiety was the monoclonal antibody to PSA, PSA10, and the particle was a magnetic particle. The magnetic particle and PSA10 were adhered to each other via a DNA linker. The linker consisted of 48 base pairs of double stranded DNA followed by 10 bases of single stranded DNA. This DNA linker was designed for this experiment to fit two types of cleavage: a non-specific cleavage with DNAse (which digests double stranded and single stranded DNA) and a specific elution with EcoRI (which digests a specific sequence of double stranded DNA). It has the advantage that it allows for a higher flexibility of the particles and enough space to enable to access of the enzymes. The data in FIG. 6 was generated with DNAse (750 units, from Qiagen). In this assay the additional step of binding a second capture moiety, which has a reagent associated with it was employed. The second capture moiety was another monoclonal antibody to PSA, PSA36, and the reagent was a magnetic bead. The recapturing of the PSA on the detection surface, here the FTIR biosensor surface of a Magnotech device, was achieved via binding of the PSA to another monoclonal PSA antibody namely PSA66. All antibodies came from Fujirebio. The reduction of the ratio of the biological sample volume to biological target, 25 pM PSA in buffer, was measured at ratios of 1:1, 1:5 and 1:10. It can be clearly seen that as the volume ratio increases the detected signal increases. Thus the reduction of the ratio of the biological sample volume to biological target leads to a concentration of the biological target prior to detection and hence to a lower signal to noise ratio, and greater sensitivity of the affinity assay.

FIG. 7A shows data of a preliminary experiment to establish a three-epitope affinity assay as described above for cardiac troponin-I (cTnI), a cardiac marker used to determine the incidence of myocardial ischemia. The biological target cTnI was pre-incubated with the first capturing moiety, 60 nM MAb2, (from BiosPacific) for ten minutes, then the solution was injected into a MagnoTech assay and the biological target cTnI bound to a second capture moiety, a-cTnI 560 (from Hytest) associated with a magnetic bead, as well as to the detection surface, here the FTIR biosensor surface of the Magnotech device. The binding of the cTnI to the detection surface was mediated via polyclonal antibodies 4T21/2 (from Hytest). The data clearly demonstrate that the binding of the first capture moiety and the second capture moiety associated with a magnetic bead do not inhibit the binding of the cTnI to the detection surface or the detection with the Magnotech device.

FIG. 7B shows data from a similar experiment to the one in FIG. 7A to establish a three-epitope affinity assay for PSA.

Figure 8:
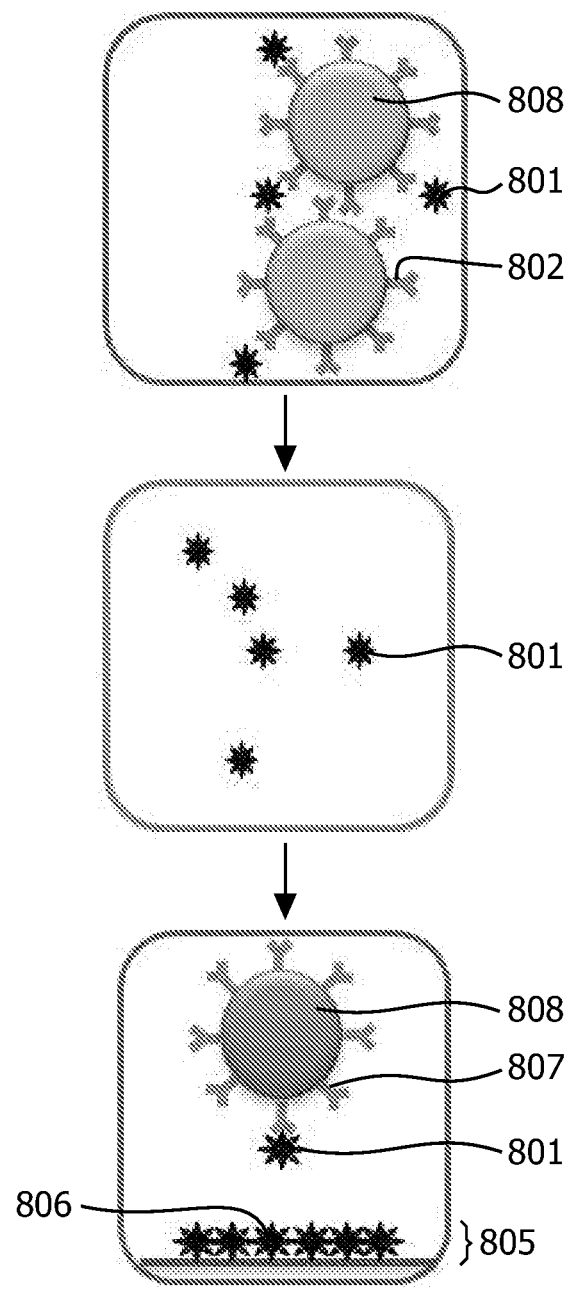
FIG. 8 shows in a schematic fashion an example for a thermal cleavage followed by a competitive affinity assay.

FIG. 8 shows in a schematic fashion an example for a thermal cleavage, in which the cleavage step of the first capturing moiety from the particle is replaced by cleavage of the biological target from the first capturing moiety. Shown are the assay steps following the concentration of the captured biological target into an elution volume that is smaller than the biological sample volume. A biological target 801 is cleaved from a first capturing moiety 802, which is adhered to a particle, here a magnetic particle, 803, through thermal cleavage and the first capturing moiety 802, adhered to the magnetic particle, 803 is removed using magnetic forces. Subsequently the biological target 801 is detected and/or quantified in a competitive assay format. The biological target 801 is recaptured by a second capture moiety 807, which has a reagent 808, here a magnetic bead, associated with it. A detection surface 805 comprises a third capture moiety 806 that is a target analogue. The presence of target 801 on capture moiety 807 reduces binding of reagent 808 to the detection surface 805 with target analogue 806. The reduced presence of reagent 808 on the detection surface 805 or inhibition of binding of reagent 808 to the detection surface 805 can, for instance, be detected via FTIR on a Magnotech device.

Figure 9:
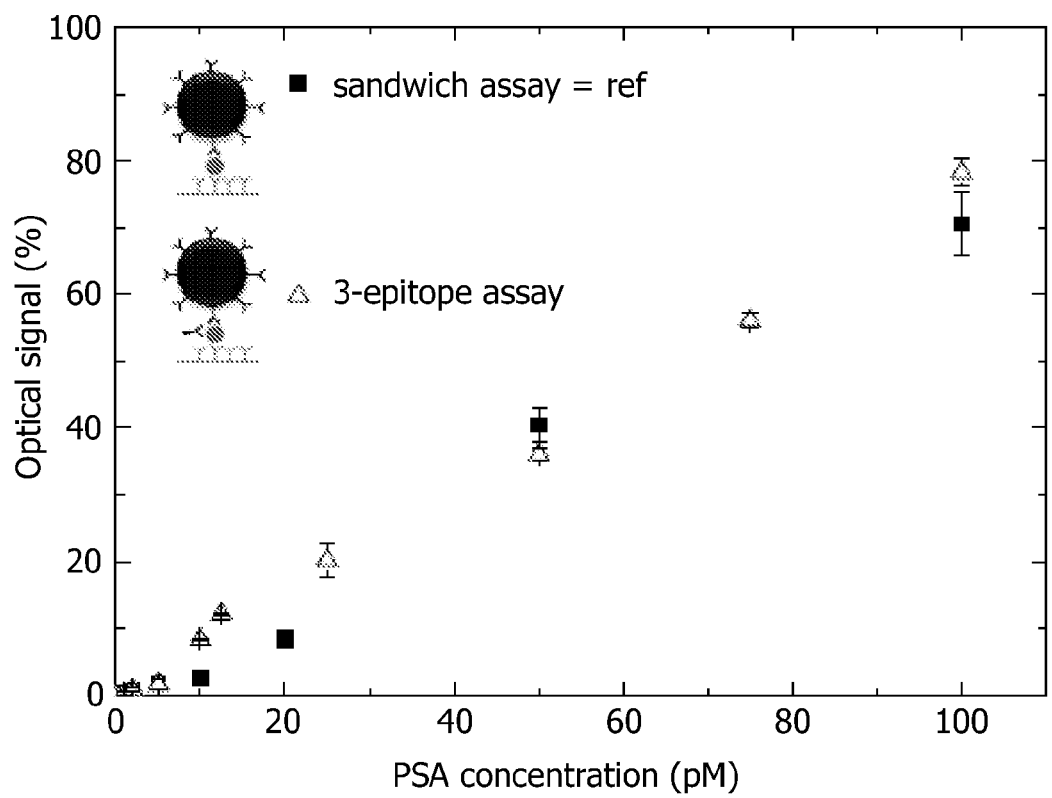
FIG. 9 shows in more detail that the first capturing moiety in a three-epitope assay does not interfere with detection.

FIG. 9 shows in more detail that the first capturing moiety in a three-epitope assay does not interfere with detection. This can already be deducted from FIG. 6 and FIG. 7. Specifically a Sandwich assay and three—epitope assay were compared to determine the impact of the first capturing moiety e.g. a third antibody on the detection. The two dose response curves are comparing the sandwich assay, generated with the PSA-10 coated beads and PSA-66 coated surface, and the three-epitope assay, obtained with PSA-36 beads on PSA-66 coated cartridge and an additional PSA-10. As both two assays have a similar dose response curve and sensitivity around 1 pM, the presence of the first capturing moiety is not hindering detection.

Figure 10:
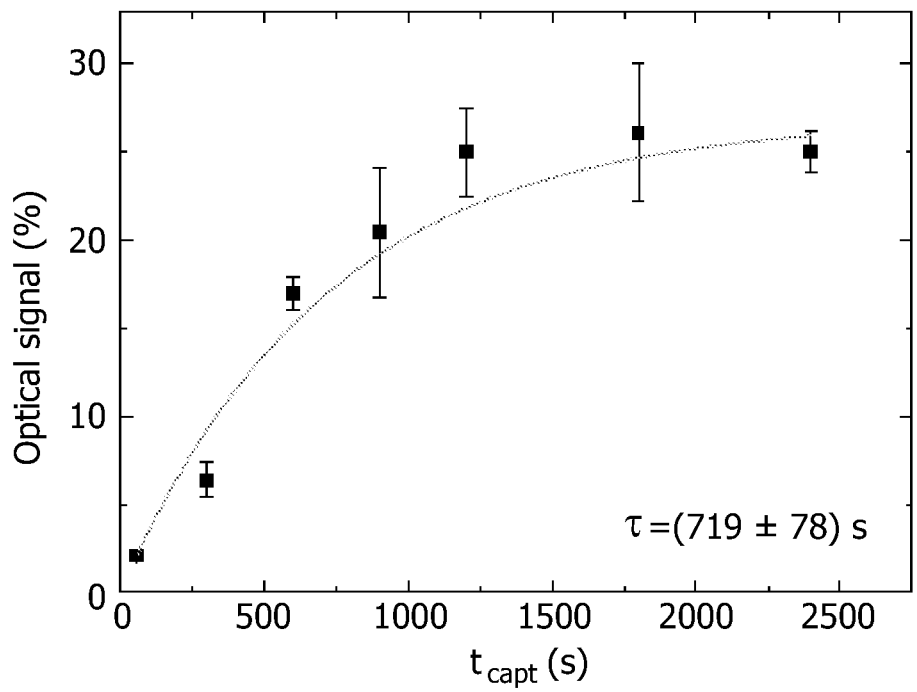
FIG. 10 shows the determination of capturing time constant.
Figure 10:
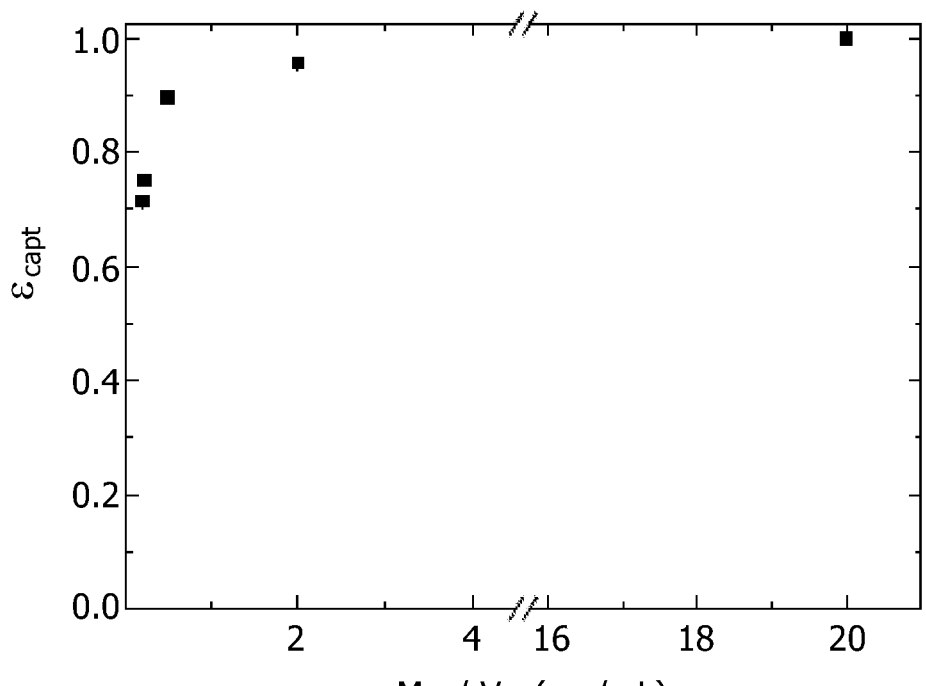

FIG. 10 shows the determination of capturing time constant. In general the first capturing reaction occurring during step b) of the method according to the invention can be investigated as a function of time and the concentration of particles. Particle concentration can be tuned to capture efficiently the biological target in a chosen time. When the particle concentration is increased, the capture is much faster. For a realistic analysis time, the enrichment process has been designed in this example not to exceed thirty minutes, while the amount of first capturing moiety was optimized at 25 µg capturing moiety per mg particle. In that prospect, the capture incubation time was fixed at fifteen minutes or 900 s. However, thirty minutes are needed to reach the equilibrium at 5 pM for 0.2 mg/mL particles in solution as shown in FIG. 10. The capture process is not a linear process but this can be simulated. The interaction between the biological target and the first capturing moiety can be simulated as a first order rate expression and after rearrangement; the capture efficiency is given by Equation I as shown above. The capture process was investigated for the following conditions: 5 µL of particles at 2 mg/mL were mixed with 45 µL PSA samples and incubated for different time until equilibrium. The results in FIG. 10 enable to estimate T as defined in Equation II, experimentally at about 720 s. τ is dependent on concentration of the first capturing moiety, and thus on particle concentration. In step b) different concentrations of particles were used. Consequently T is changing for each concentration of particles. The capture efficiency could be then determined for each particle concentration as shown in FIG. 10b.

FIG. 11 shows an enrichment assay for various volumetric enrichment factors in a total assay time of 30 min. The optical signal is plotted versus the end concentration of PSA in pM. Different volumetric ratios were used for the enrichment, the biological sample volume varied from 5 to 400 µL while the elution volume was fixed at 5 µL.

In this example concentration of the captured biological target into an elution volume was carried out with enzymatic elution to keep the process independent of the biological target e.g. protein of interest. The enzyme was used in this example to cleave the linker between the particles and the antibodies. The method was carried out 30 minutes including 15 minutes for step b of the method according to the invention, 10 minutes for steps c and d according to the invention, 5 minutes and 30s for step e). An enrichment of the signal compared to the reference dose response curve was obtained for a range of PSA between 0 and 50 pM as shown in FIG. 11. The enrichment dose response curves are differentiated by the ratio between the biological sample volume ($V_S$) as a starting volume of PSA and the elution volume ($V_{el}$). The biological sample volume varied from 5 to 400 µL. The biological sample was mixed with 0.01 mg of particles, which were concentrated to 5 µL. The eluate was detected on the biosensor. The enrichment factor (ξ) was obtained from FIG. 11 by calculating the ratio of the slope of the dose response curve obtained by enrichment assay over the slope of the dose response curve of the reference. FIG. 11 shows that the sample is effectively concentrated when the volume ratio is over a factor ten. The increase in sensitivity is consistent with the increase in volume ratio.

Figure 12:
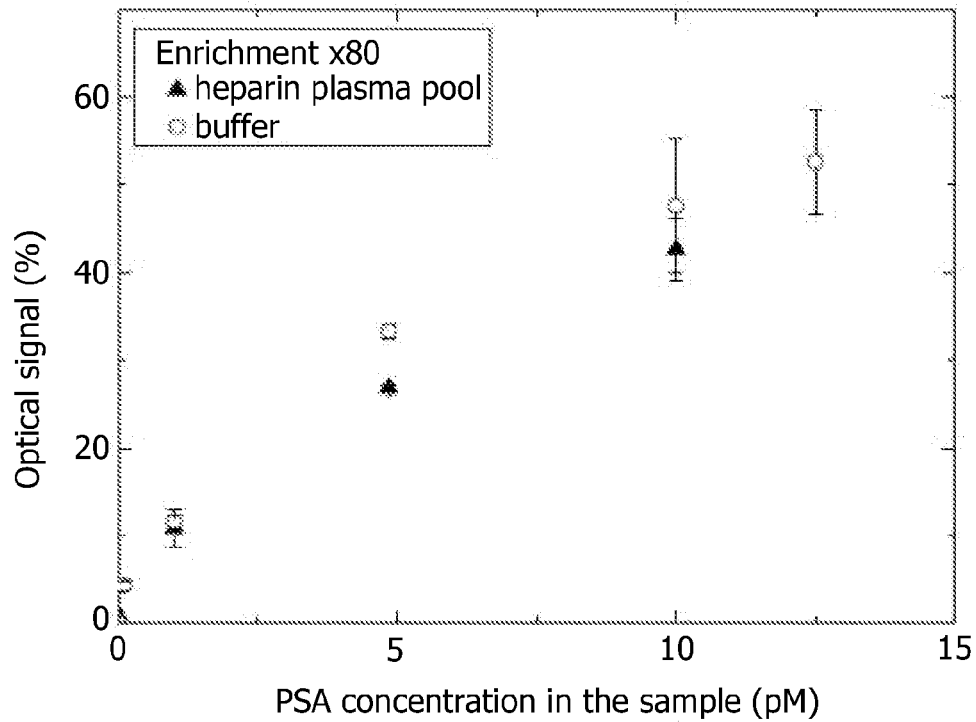
FIG. 12 shows a dose response curve of step c), i.e. of the concentration of a biological target.

FIG. 12 shows a dose response curve of step c) i.e. of the concentration of biological target. In this example a heparin plasma pool was compared to the dose response curve in buffer for a total assay time of 30 minutes. In this example, the concentration of biological target in combination with enzymatic elution has the potential in a biological matrix to clean efficiently the plasma as non specific protein cannot be eluted with the enzyme. FIG. 12 demonstrated that the enrichment is feasible in a heparin plasma pool where the target has been spiked in. The plasma was first depleted with anti-PSA particles to make sure that the pool was free of PSA. The sample was first depleted and then an accurate concentration of PSA was spiked in. To avoid dilution, the particles were re-suspended directly in plasma ($V_P$=0) and the contact of the particles with plasma was large. The slope obtained in plasma is in the same range as the one obtained in buffer for enrichment ×80 as shown in FIG. 12. The two matrices showed surprisingly a similar sensitivity.

This is meaningful as for recurrence of prostate cancer, the range of PSA targeted is actually lower than healthy donor, which is generally comprised between 10 and 20 pM. In buffer the assay at ×80 of FIG. 12 showed saturation between 10 and 20 pM. PSA tests target a range from 0.01-100 ng/ml, with a grey zone for diagnostics of cancer from 4 to 10 ng/mL. Nevertheless, recurrence case in prostate cancer showed the need for a highly sensitive test. The case of PSA is interesting because with the concentration of captured biological target, it was shown that the sensitivity could be shifted to detect recurrence of the cancer after biopsy. Thus, for the same detection platform, an assay could be enriched and be adaptable for two applications: general monitoring and a highly sensitive assay.

EXAMPLES

Materials

All buffer materials unless otherwise stated were supplied by Sigma Aldrich Corporation. Superparamagnetic particles functionalized with carboxylic acid groups (MasterBeads 500 nm diameter) were purchased from Ademtech. A number of antibody pairs recognizing various epitopes on PSA were screened and found to be very effective for the detection of PSA using the optomagnetic biosensor technology. In this work we focus on results from the pair consisting of the monoclonal antibody PSA-10 as a capture antibody, PSA-36 as a second recapture antibody and PSA-66 as the capture antibody immobilized on the sensor surface. The antibodies are provided by Fujirebio. Calibrators were prepared from human PSA complex (Fujirebio PSA kit) by diluting either in pure human heparin plasma pool from 20 apparently healthy donors or in 5% BSA in PBS (for buffer experiments). DNase was purchased from Qiagen and diluted in sterile RNAse free water. NEB EcoRI buffer ×10 concentrated was supplied by NEBiolabs was used as elution buffer. Antibodies were conjugated using 1-ethyl-3-(3-dimethylaminopropyl)carbodiimide (EDC, Sigma Aldrich) chemistry in 1× phosphate buffered saline (PBS) for 1 hour at room temperature with shaking. The conjugates were purified with a TSK-Gel SuperSW 3000 column (Tosoh Biosciences, 300×4.6 mm, 4 μm particles, 25 nm mean pore size), run at a flow rate of 0.25 mL 60 mM phosphate buffer, pH 6.8, per minute at ambient temperature, monitored at 260 and 280 nm. Capture beads were prepared as followed: a mixture of 1:1 streptavidin beads at 2 mg/mL coupled with 500 nM DNA coupled PSA-10 IgG was incubated for 20 minutes. Then, the beads were washed and re-suspended at 2 mg/mL in 5% BSA in PBS. 50 μL capture beads at 2 mg/ml were mixed with PSA sample for 15 minutes, then the beads are washed magnetically and re-suspended in 1:1 DNase and NEB EcoRI ×1. After 10 minutes elution, the beads were removed magnetically. 3.5 μL eluate and 3.5 μL PSA-36 coated magnetic beads at 2 mg/mL were mixed and directly injected in the disposable cartridge.

Example 1

Figure 7:
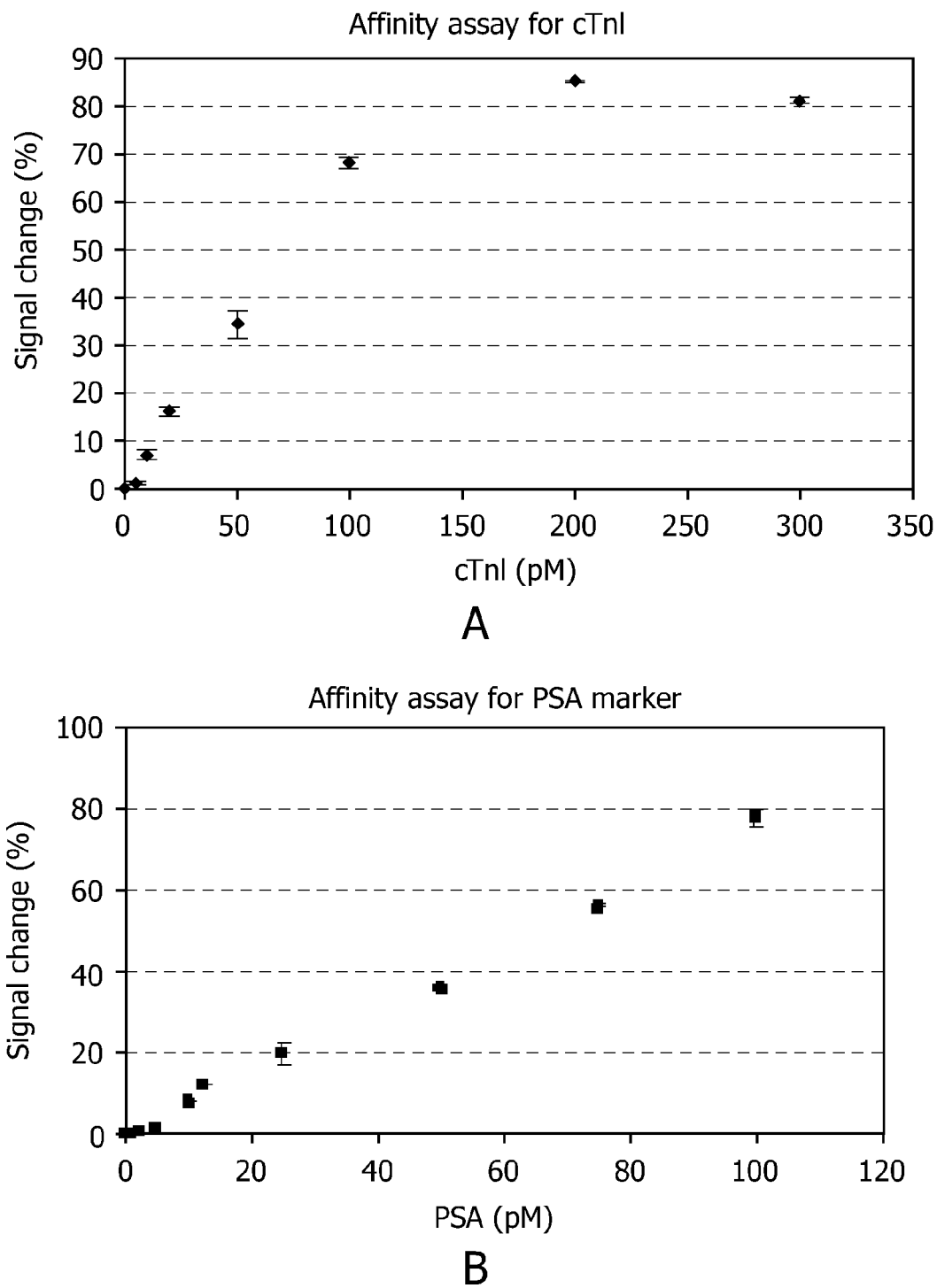
FIG. 7 shows data from preliminary experiments to establish a three-epitope affinity assay for cardiac troponin-I (cTnI) and for prostate-specific antigen (PSA).

The affinity assay according to the invention was, in addition to the experiments shown in FIG. 6 and FIG. 7, also carried out using thermal cleavage. For this experiment opiate (DB1327 from Cerillian) at 30 ng/mL was used as the biological target, the first capturing moiety was a morphine-3 antibody from NatuTec and the particle was a magnetic particle. The thermal cleavage step was tested at a range of temperatures ranging from 50° C. to 95° C., with 80° C. giving the best results. Recapturing of the biological target on a detection surface occurred by capturing the opiate on a FTIR biosensor surface coated with BSA and opiate and detection was carried out in a MagnoTech device using a second capturing moiety, again the morphine-3 antibody from NatuTec associated with magnetic particles. It was clearly demonstrated that the thermal cleavage released the target from the first capturing moiety.

The device, methods and systems described in the present invention can be used for rapid, robust, and easy to use point-of-care biosensors. The reaction chamber can be a disposable item to be used with a compact reader containing the one or more detection means. Also, the device, methods and systems of the present invention can be used in automated high-throughput testing. In this case, the reaction chamber is, e.g., a well plate or cuvette, fitting into an automated instrument.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. The mere fact that certain measures are recited in mutually different dependent claims does not indicate that a combination of these measures cannot be used to advantage. Any reference signs in the claims should not be construed as limiting the scope.

Example 2

The capture efficiency was determined by the capture process fitting as explained above in FIG. 10. Consequently the elution efficiency could be derived from the equation II as summarized in Table 1. FIG. 11 was used to determine the experimental data stated in the Table 1, then the enrichment efficiency was derived from the slope of the dose response curves from FIG. 11 and the elution efficiency was derived.

TABLE 1

Enrichment assay table corresponding to FIG. 11. The enrichment efficiency is the ratio of the slope of the enrichment dose response curve over the slope of the dose response curve of reference. The capture efficiency was calculated from the equation I. From the volumetric enrichment, the enrichment efficiency and the capture efficiency, the elution efficiency was determined.

| | Experimental parameters | | | | | | | Experimental results | | | |
|---|---|---|---|---|---|---|---|---|---|---|---|
| Curves | $V_S$ (μL) | $V_P$ (μL) | $m_P$ (mg) | $V_{capt}$ (μL) | $V_{el}$ (μL) | $m_L$ (mg) | $\epsilon_{conc} = V_S/V_{el}$ | Slope (% per pM) | $\zeta$ | $\epsilon_{capt}$ | $\epsilon_{el}$ |
| ref | 5 | — | — | 10 | — | 0.01 | — | 0.410 ± 0.008 | — | — | — |
| x1 | 5 | 5 | 0.1 | 10 | 5 | 0.01 | 1 ± 0.02 | 0.118 ± 0.009 | 0.29 ± 0.05 | 1 ± 0.001 | 0.29 ± 0.08 |
| x10 | 50 | 50 | 0.1 | 100 | 5 | 0.01 | 10 ± 0.2 | 1.19 ± 0.08 | 2.91 ± 0.16 | 0.96 ± 0.16 | 0.30 ± 0.07 |
| x40 | 200 | 50 | 0.1 | 250 | 5 | 0.01 | 40 ± 1 | 5.07 ± 0.71 | 12.37 ± 0.71 | 0.89 ± 0.18 | 0.35 ± 0.14 |
| x80 | 400 | 50 | 0.1 | 450 | 5 | 0.01 | 80 ± 2 | 6.09 ± 0.52 | 14.86 ± 0.52 | 0.75 ± 0.27 | 0.25 ± 0.09 |

This clearly showed the dependence of the enrichment efficiency in function of time or sample volume or elution efficiency depending on the constraints applied on the method. For a short capture time (t<<τ), the enrichment efficiency is directly related to the capturing time, the elution efficiency and the elution volume. For a capture time larger or equal to τ, the enrichment efficiency is directly related to the sample volume and the elution efficiency. As shown in Table 1 for 900s the enrichment efficiency is dependent on the sample volume and the elution efficient. The capture efficiency is changing in proportion to the sample volume. Consequently the derived elution efficiency was found in the same range for each enrichment factor about 30%. For this set of data the amount of particles was kept constant. Therefore, it is believed that the elution efficiency is directly linked to the amount of particles in the biological sample volume. This was confirmed by two simple experiments: the elution was carried out on a gel and the elution was also carried out on a smaller amount of particles. In the first attempt, on a gel, without beads, the same proportion of DNA linkers was eluted at 98% (±5%) in 10 minutes. In the second experiment, ten times less particles were used in the enrichment. Considering a change in capture efficiency (from 100% to 92%), the elution efficiency was found in that case at 70%. Consequently, the more particles are added during the elution, the lower the elution efficiency is. This lead to believe that two phenomena are competing during elution: the chemical reaction and the diffusion. In conclusion, the process is stable and reproducible. Nevertheless, the enrichment assay can be improved if the diffusion factor is improved.

In summary of the Figures and examples it was demonstrated that the method according to the invention can be applied to concentrate a biological target for example for immunoassay detection. Compared to the traditional methods in sample preparation, this assay showed a similar or better recovery and a more favorable adaptation for immunoassay detection. The assay slope showed an increase by a factor eighteen with optimized parameters with a volume enrichment of eighty. The method can be achieved in thirty minutes prior to detection and still and a factor fifteen improvement can be noticed. The process is also effective in full plasma. This combination of a good recovery and potential of enrichment to reach a high sensitivity makes this process a very promising method for protein analysis in a miniaturized format including purification, enrichment and detection.

The invention claimed is:

1. A method for detecting prostate-specific antigen in an affinity assay, the method comprising the steps of:
    a) providing a biological sample volume containing the prostate-specific antigen at a concentration of from at 4 to 10 ng/ml;
    b) adding PSA-10 antibody capturing moiety to the biological sample volume, wherein the PSA-10 antibody capturing moiety captures the prostate-specific antigen and is adhered to a magnetic particle, wherein the PSA-10 antibody capturing moiety is linked to the particle via a linker comprising a DNA linker consisting of 48 base pairs of double stranded DNA followed by 10 bases of single stranded DNA, wherein the DNA is digestable by a DNAse and cleavable for specific elution with EcoRI;
    c) concentrating the captured prostate-specific antigen by magnetic particle separations into an elution volume of less than 5 µL that is at least eighty times smaller than the biological sample volume in step a) in a time of fifteen minutes;
    d) cleaving the prostate-specific antigen from the particle, wherein at least 30% of the prostate-specific antigen is cleaved from the particle using a DNAse or EcoRI;
    e) binding the prostate-specific antigen to a modified PSA-36 antibody capturing moiety associated with a reagent and to a modified PSA-66 antibody capturing moiety comprising a tag, wherein a portion of the PSA-10 antibody capturing moiety that was cleaved from the particle binds to one of the modified antibodies, and
    f) at least one of detecting and quantifying the prostate-specific antigen in an affinity assay format, wherein the tag binds to a fourth capturing moiety on a detection surface.

2. The method according to claim 1, wherein the reagent is selected from the group consisting of:
    a radioisotope,
    a solid phase,
    a fluorescent, phosphorescent, or chemiluminescent dye,
    an enzyme or enzyme substrate,
    a nucleic acid sequence or peptide,
    a colloid or nanoparticle, and
    a polymer or macromolecule.

3. The method according to claim 1, wherein the at least one of detecting and quantifying step e) is performed according to a method selected from the group consisting of:
    an optical detection,
    an enzyme reaction,
    nucleic-acid amplification techniques,
    a magnetic detection,
    a sonic detection, and
    an electrical detection.

4. The method according to claim 1, wherein the tag comprises biotin and the fourth capturing moiety comprises either avidin or streptavidin.

5. A method for detecting prostate-specific antigen in an affinity assay, the method comprising the steps of:
    a) providing a biological sample volume containing the prostate-specific antigen at a concentration of from at 4 to 10 ng/ml;
    b) adding PSA-10 antibody capturing moiety to the biological sample volume, wherein the PSA-10 antibody capturing moiety captures the prostate-specific antigen and is adhered to a magnetic particle, wherein the PSA-10 antibody capturing moiety is linked to the particle via a linker comprising a DNA linker consisting of 48 base pairs of double stranded DNA followed by 10 bases of single stranded DNA, wherein the DNA is digestable by a DNAse and cleavable for specific elution with EcoRI;
    c) concentrating the captured prostate-specific antigen by magnetic particle separations into an elution volume of less than 5 µL that is at least eighty times smaller than the biological sample volume in step a) in a time of fifteen minutes;
    d) cleaving the prostate-specific antigen from the particle, wherein at least 30% of the prostate-specific antigen is cleaved from the particle and wherein the cleavage is enzymatic;
    e) binding the prostate-specific antigen to a modified PSA-36 antibody capturing moiety associated with a reagent and to a modified PSA-66 antibody capturing moiety comprising a tag, wherein a portion of the PSA-10 antibody capturing moiety that was cleaved from the particle binds to one of the modified antibodies, and f) at least one of detecting and quantifying the prostate-specific antigen in an affinity assay format, wherein the tag binds to a fourth capturing moiety on a detection surface.

6. A method for detecting prostate-specific antigen in an affinity assay, the method comprising the steps of:
a) providing a biological sample volume containing the prostate-specific antigen at a concentration of from at 4 to 10 ng/ml;
b) adding PSA-10 antibody capturing moiety to the biological sample volume, wherein the PSA-10 antibody capturing moiety captures the prostate-specific antigen and is adhered to a magnetic particle, wherein the PSA-10 antibody capturing moiety is linked to the particle via a first entity for attachment to a particle comprising a DNA linker, wherein the DNA is digestable by a DNAse and cleavable for specific elution with EcoRI;
c) concentrating the captured prostate-specific antigen by magnetic particle separations into an elution volume of less than 5 µL that is at least eighty times smaller than the biological sample volume in step a) in a time of fifteen minutes;
d) cleaving the prostate-specific antigen from the particle, wherein at least 30% of the prostate-specific antigen is cleaved from the particle using a second entity for the cleavage of the attachment to the particle;
e) binding the prostate-specific antigen to a modified PSA-36 antibody capturing moiety associated with a reagent and to a modified PSA-66 antibody capturing moiety comprising a third entity for attachment to a detection surface, wherein a portion of the PSA-10 antibody capturing moiety that was cleaved from the particle binds to one of the modified antibodies, and
f) at least one of detecting and quantifying the prostate-specific antigen in an affinity assay format, wherein the third entity binds to a fourth capturing moiety on a detection surface.

* * * * *